United States Patent [19]

Beauvoir

[11] 3,981,867
[45] Sept. 21, 1976

[54] PROCESS FOR OBTAINING SAPOGENIN PARTICULARLY HECOGENIN FROM PLANT MATERIAL SUCH AS AGAVE SISALANA LEAVES

[76] Inventor: Max G. Beauvoir, P.O. Box 2187, Port-au-Prince, Haiti

[22] Filed: Mar. 17, 1975

[21] Appl. No.: 559,012

[52] U.S. Cl. .................................. 260/239.55 A
[51] Int. Cl.[2] .................................. C07J 17/00
[58] Field of Search ...................... 260/239.55 A

[56] References Cited
UNITED STATES PATENTS

| | | | |
|---|---|---|---|
| 3,136,761 | 6/1964 | Loken | 260/239.55 A |
| 3,449,328 | 6/1969 | Hardman | 260/239.55 A |
| 3,505,316 | 4/1970 | Belter et al. | 260/239.55 A |

*Primary Examiner*—Elbert L. Roberts

[57] ABSTRACT

An improved process for obtaining sapogenins, mainly hecogenin, from plants. This improved process involves collecting, undiluted, the juice of sisal leaves and subjecting this juice to acid hydrolysis at elevated temperature and pressure. The sapogenin fraction is then recovered as crude hecogenin, which constitutes a water insoluble reaction product in the hydrolyzate. This is further purified by extraction with an appropriate organic solvent to yield a high quality crystallizable mixture of hecogenin and tigogenin. From this mixture of sapogenin the hecogenin is separated further from the tigogenin by preferential acetylation and recrystallization.

14 Claims, 4 Drawing Figures

INFRA RED SPECTRA OF PRODUCT SAMPLES

PROCESS FOR OBTAINING SAPOGENIN PARTICULARLY HECOGENIN FROM PLANT MATERIAL SUCH AS AGAVE SISALANA LEAVES

BACKGROUND OF THE INVENTION

1. Field of the Invention

This present invention relates to an improved method for producing steroidal sapogenins such as hecogenin from leaves of plants such as *Agave sisalana*. A sapogenin is a constituent of saponins; sapogenins occur naturally in the juice of certain plants in the form of the appropriate water soluble saponin. A saponin is a member of a group of glycosides, some steroidal derivatives, which are usually characterized by their property of producing a soapy lather. Chemically they consist of multiple sugar groups linked to a sapogenin nucleus by means of a glycosidic bond.

Among the sapogenins, hecogenin is of prime importance in the synthesis of corticoids. It is used as a raw material in the production of such cortical hormones as cortisone, cortisol, prednisolone, prednisone, dexamethasone, betamethasone, triamcinolone and others. Its usefulness as a synthetic starting material is due to the fact that hecogenin possesses an oxygen atom in the C-12 position which can be moved to the C-11 position. This makes it possible to introduce the 9–11 double bond which is necessary for the syntheses of the above mentioned hormones, as shown in the synthetic pathway set out in FIG. 1, described more fully hereinafter.

2. The Prior Art

As a means of obtaining crude hecogenin some prior art references disclose a fermentation process. Others describe hydrolysis at atmospheric pressure. Still others couple both of these techniques, and some even suggest the use of alcohol as a precipitating agent. Generally the use of large quantities of acid is advocated. I have found the above mentioned art unsatisfactory for the following reasons:

1. The use of large amounts of acid results in charring the plant juice; the resulting crude hecogenin is usually black and even shows the presence of calcium sulfate crystals. Also, the hecogenin yield is usually very poor.
2. The use of alcohol as a precipitating agent is very unsatisfactory since the reaction is accompanied by violent bumping.
3. The use of biological fermentation is a long and tedious process with reaction time varying between two days and a week, necessitating the use of extremely large storage vats.
4. When acid hydrolysis is used at low pressure, I have found it necessary to run the hydrolysis overnight in order to obtain 50 to 70% of the expected hecogenin yield.

It is obvious to those skilled in the art that such operations as those described above are inefficient and time consuming, and produce very expensive hecogenin, which, from an economic viewpoint alone, limits their use.

THE DRAWINGS

SUMMARY OF THE INVENTION

Figure 1:
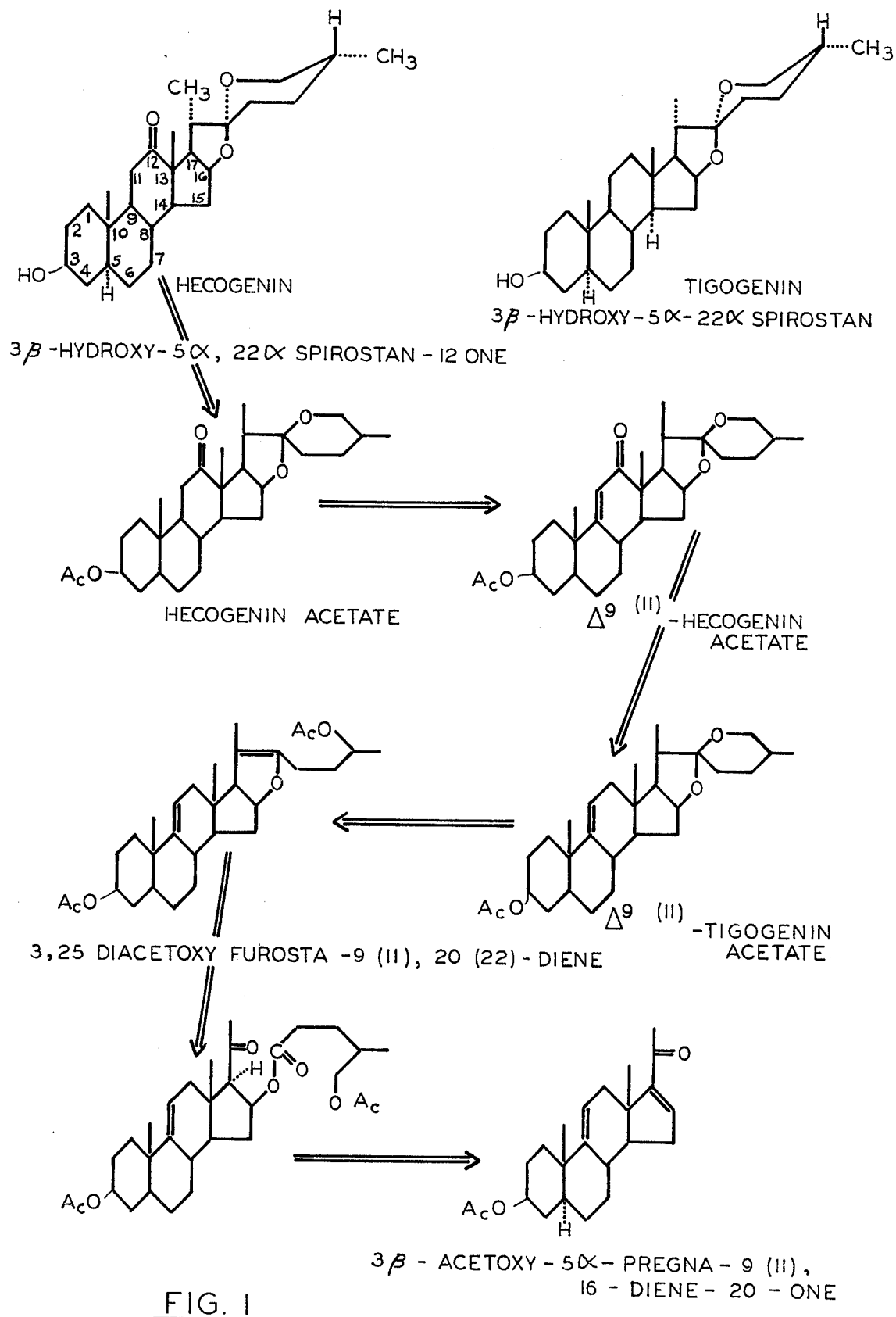
FIG. 1 is a drawing of the chemical pathway from hecogenin, the product of the claimed process, to 3$\beta$-acetoxy-5$\alpha$-pregna-9(11), 16-diene-20-one. The structure of tigogenin is also shown.

One benefit of the present invention is that this process makes available very large quantities of inexpensive hecogenin which is useful in producing the cortical hormones above mentioned. Furthermore, this hecogenin may also compete successfully against diosgenin, which is obtained from the dwindling supplies of dioscoreaceae and which is used to produce birth control steroid pills such as oestrogens, progestogens, 19-norsteroids, etc.

The present invention is a process for obtaining sapogenin, mainly hecogenin, from plants containing those substances. This improved process is more efficient and produces larger and cheaper quantities of sapogenin and hecogenin than the processes of the prior art. The steps of the process of the present invention include an acid hydrolysis reaction carried out at a pH in the range of 0.4 to 1.5. The liquor undergoing hydrolysis is heated to between 150° C. and 250°C. and kept under pressure in the range of 40 to 125 p.s.i.g. After between 45 minutes and three hours of reaction time, the sapogenin is recovered as "crude hecogenin" by any separation method, such as filtration, since the "crude hecogenin" constitutes a water insoluble reaction product in the hydrolyzate. Further purification of the "crude hecogenin" is accomplished by extraction with an appropriate organic solvent to yield a high quality crystallizable mixture of hecogenin and tigogenin. From this mixture of sapogenin the hecogenin is separated further from the tigogenin by preferential acetylation and recrystallization. The preferred source material is the juice of *Agave sisalana*; the preferred acid is sulfuric acid; the preferred hydrolysis condition is 60 p.s.i.g. for 90 minutes at pH 0.5 and 180° C. The preferred organic solvent for the sapogenin extraction is heptane.

PREFERRED EMBODIMENT

The principle of the method of the present invention is as follows:

Sisal leaves are usually decorticated with large amounts of water, on the order of 200 to 500 gallons per minute. For economic reasons, which should be obvious to those skilled in the art, as well as for ease of handling, I suggest the discontinuation of the use of water in the decortication process. Instead, the juice should be collected virgin, i.e., undiluted. This is accomplished using a 2000 gallon reservoir located very close to the decorticator. This reservoir should be filled with an initial quantity of virgin juice obtained from dry decortication. This auxiliary supply of juice is then recirculated over and over on the decorticator, replacing the water originally used. The overflow of the reservoir, after being strained, should be sent to a larger vat, capable of storing in gallons eight times the number of kilograms of fiber produced in 2 days. This juice is then processed for hecogenin. The strained material, generally called bagasse, which is composed of pulp, skin, wax and short fibers, is pressed through a squeeze roller, or more preferably homogenized. The extra juice obtained by pressing the bagasse increases significantly the final yield of hecogenin.

The juice, free from all debris, is then sent to a reactor. This reactor should be either a glass-lined or stainless steel vessel, capable of accepting at least 60 pounds of working pressure. For convenience, I suggest that the reactor be large enough to hold 15 to 25% of the daily juice production, since the reaction time is approximately 2 hours.

The pH of the juice is then adjusted to within a range of 0.4 to 1.5, preferably from pH 0.4 to 0.6. This pH adjusted juice should contain considerable amounts of buffers, as would be understood by one skilled in the art. Even though 5 to 50 grams of sulfuric acid per liter of juice may be used, on a practical level I have found a ratio of 25 grams of sulfuric acid per liter of juice quite satisfactory. However, it should be understood that any mineral acid will yield good crude hecogenin.

The use of hydrochloric acid offers the advantage that it is easily removed when the crude hecogenin is dried, since it will evaporate out. However, the cost of hydrochloric acid and the difficulties one encounters in handling it make sulfuric acid the preferred acid. Although sulfuric acid is the preferred acid, one must be careful when using it since it may char the material if it is not thoroughly washed out prior to drying.

Phosphoric acid is the preferred acid if the neutralized liquor obtained after hydrolysis is to be used for cultivation, as a fertilizer substitute. The neutralized liquor may be so utilized since the juice contains:

| | |
|---|---|
| Sugar | 131 mg per 100 ml |
| Nitrogen | 50.3 mg per 100 ml |
| Urea Nitrogen | 107.6 mg per 100 ml |
| Phosphorous | 441 mg per 100 ml |
| Protein | 3.6 mg per 100 ml |
| Calcium | 106.2 mg per 100 ml |
| Potassium | 57 milli equivalent per liter |
| Specific gravity | 1.038 |

It should be noted from the above table that the mother liquor which is obtained from the hydrolysis reaction is rich in nitrogen, phosphorous and potassium and thus can readily be used as a fertilizer substitute or as an additive to an already existing fertilizer. This mother liquor is also rich in sugar; this sugar may be extracted by standard technique and then used to produce ethanol and yeast by processes well known in the art. Moreover, furfural, which is formed during the hydrolysis, can be extracted using standard techniques of separation and extraction.

Figure 2:
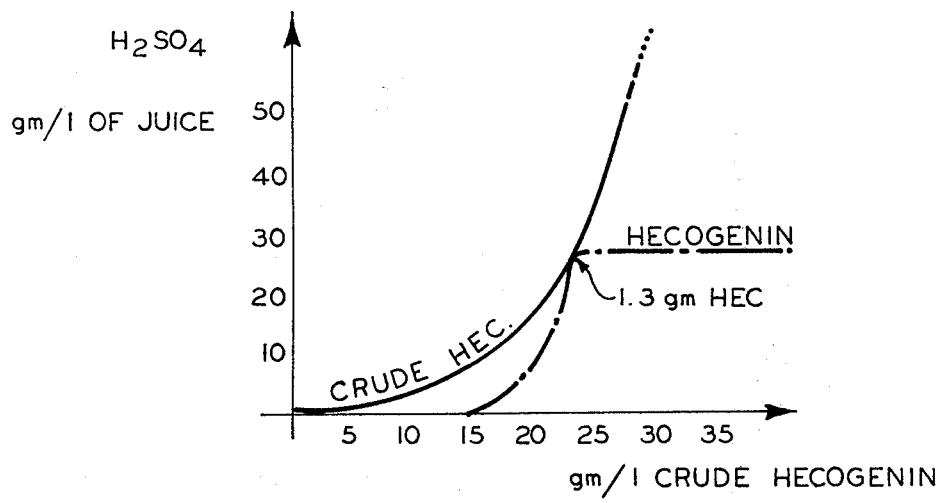
FIG. 2 illustrates the change in yields of crude hecogenin and hecogenin in grams per liter of juice with changing sulfuric acid concentration in grams per liter of juice. Other conditions are the preferred operating conditions.
Figure 3:
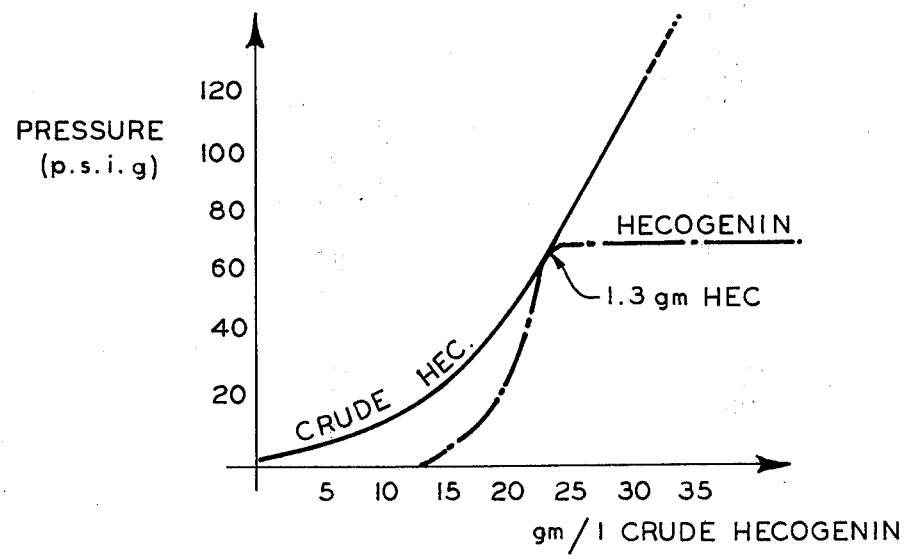
FIG. 3 illustrates the change in yields of crude hecogenin and hecogenin in grams per liter of juice with changing pressure in p.s.i.g. Other conditions are the preferred operating conditions.

The hydrolysis is then allowed to proceed within a pressure range of 40 to 125 p.s.i.g. for 45 minutes to 3 hours at a temperature between 150°C. and 250° C. Although the yield of crude hecogenin can be increased by varying any one parameter, the system of choice for the production of crude hecogenin is 25 grams sulfuric acid per liter of juice maintained in the reactor at 60 p.s.i.g. for 90 minutes at 180° C. These preferred conditions offer at a later stage the highest yield of pure hecogenin. See the graphs for FIGS. 2 and 3. The benefit of the above mentioned conditions is that a lower dilution of the hecogenin in the crude hecogenin is obtained which is advantageous at the time of extraction.

After about 90 minutes of hydrolysis the reactor is cooled and the crude hecogenin is separated from the hydrolyzate by any convenient means of separation, such as filtration, centrifugation or decantation.

The solid hydrolyzate collected as crude hecogenin, which contains hecogenin and tigogenin, is washed with ample amounts of ordinary tap water to remove all traces of acid. The solid hydrolyzate is then dried, preferably in an oven at 80° to 100° C. until the crude hecogenin contains only 3 to 5% moisture.

This neutral, dry, crude hecogenin can then be bagged and stored for long periods of time or refined by extraction.

The yield of crude hecogenin obtained from the same plantation was very reproducible from sample to sample. Variations in replications and in duplications were less than 5%, which is well within the limits of experimental error.

The following results, plus or minus 5%, were obtained from different sisal plantations:

| | | | Crude Hecogenin | |
|---|---|---|---|---|
| Fort Liberts | 25,000 | acres | 23.5 | gms/liter |
| Terrier Rouge app. | 5,000 | acres | 17.5 | gms/liter |
| Saintare | 7,500 | acres | 14.13 | gms/liter |
| Carries | 5,000 | acres | 22.0 | gms/liter |
| Doko-Williamson | 5,000 | acres | 8.6 | gms/liter |
| Fond-Grand-Martin | 5,000 | acres | 8.1 | gms/liter |
| Bois Neuf | 7,000 | acres | 21.3 | gms/liter |
| La Gonave | 10,000 | acres | 18.3 | gms/liter |
| Marie Gerbo | 3,000 | acres | 30.4 | gms/liter |
| Shada | 5,000 | acres | 10.9 | gms/liter |
| Nadal | 5,000 | acres | 36.1 | gms/liter |
| Grand Goave | 1,000 | acres | 15.3 | gms/liter |
| Miragoane | 5,000 | acres | 17.2 | gms/liter |
| Cotes de Fer | 8,000 | acres | 18.5 | gms/liter |

The extraction of hecogenin and tigogenin from the crude hecogenin may be most easily carried out using any one of the following hydrocarbon solvents: xylene, toluene, benzene, naphtha, heptane, octane, hexane, cyclohexane and the like. Methyl alcohol and ethyl alcohol have also been suggested in previous literature.

I have found this extraction to be better effected in a soxhlet type apparatus, using heptane as the preferred solvent. The extraction is complete in 2 to 3 hours depending on the ratio of heptane to crude hecogenin. Generally, 50 to 100 grams of crude hecogenin per liter of heptane is sufficient. After the extraction the soxhlet is replaced by a distilling apparatus which allows for removal of pure heptane. Approximately 40 to 50 ml of heptane is left in the still to dissolve one gram of expected hecogenin.

The solution of sapogenin is then cooled at room temperature for 2 to 4 hours, allowing the sapogenin to crystallize.

It is then collected on a porous and adsorbing surface, washed with cold heptane, and dried in an oven at 80° C. for 20 minutes. This latter operation not only dries the sapogenin but it also removes any traces of wax that were extracted along with it.

Hecogenin may be separated from tigogenin by the standard techniques of preferential acetylation and recrystallization.

Figure 4:
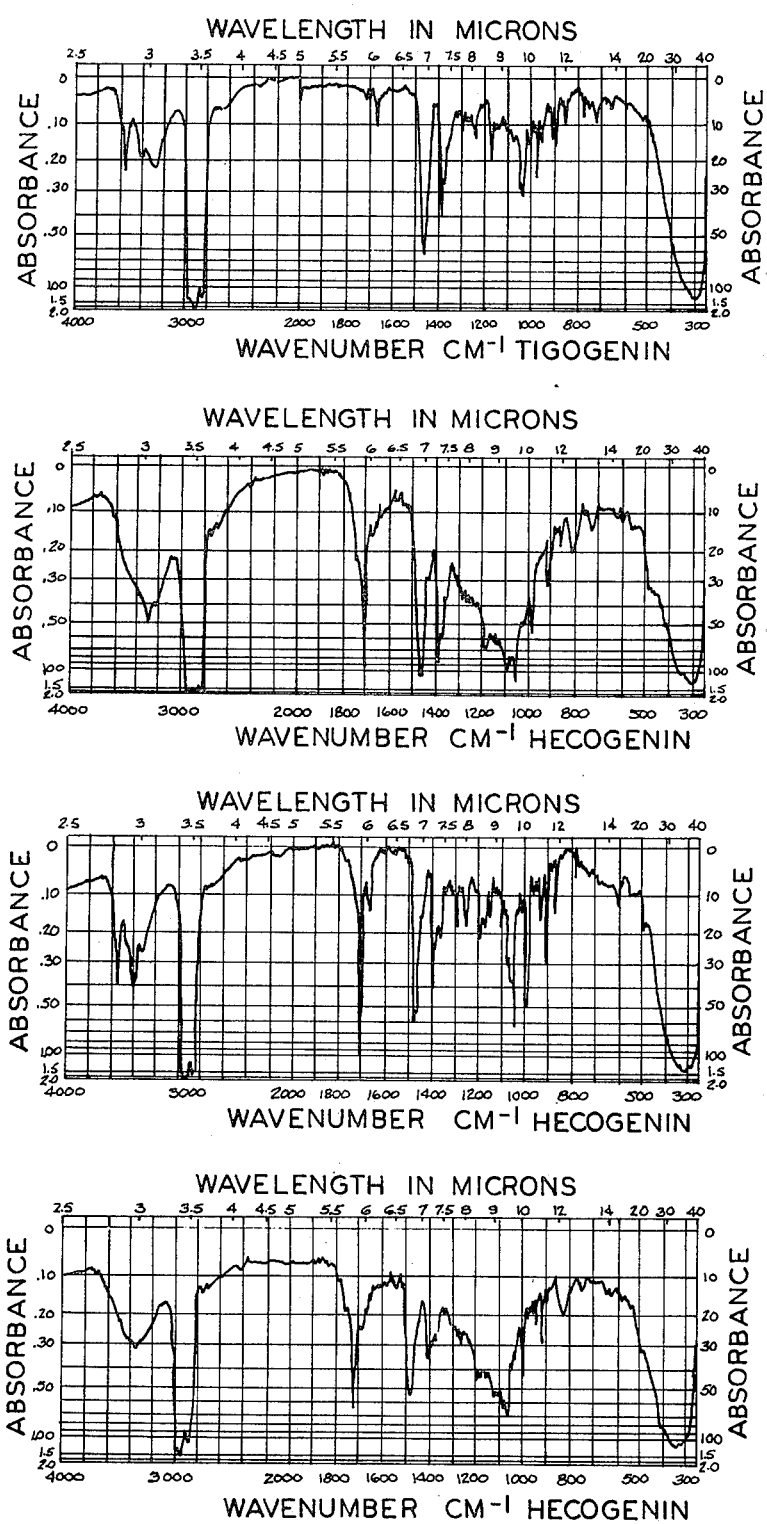
FIG. 4 is a reproduction of infra red absorption spectra of the product of the claimed process, and of chromatography results showing the percentages of hecogenin and tigogenin in representative product samples.
Figure 4:
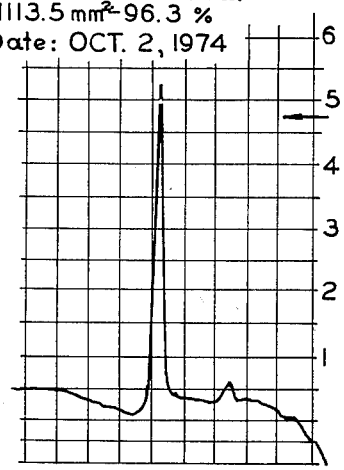
Figure 4:
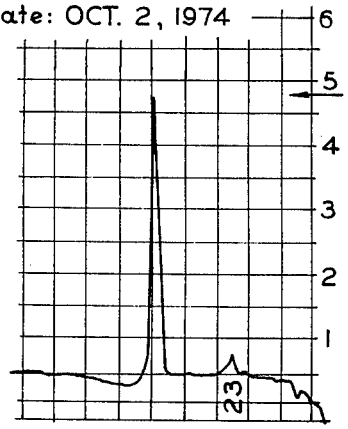

The yield of sapogenin from the juice has been found to be 1.3 to 1.4 grams per liter, of which 94.58% is hecogenin and 5.5% is tigogenin. See FIG. 4.

Using mass spectrometry the molecular weights of tigogenin and hecogenin were identified as 416 and 430 grams respectively.

Numerous variations from the specific details described above may be employed without departing either from the spirit of the present invention or the scope of the appended claims.

I claim:

1. A process for obtaining steroid content from saponin-containing juices of certain plant material, which process comprises:

acidifying said juices to a pH of from 0.4 to 1.5 with an acid selected from the group consisting of sulfuric, hydrochloric and phosphoric acids;

subjecting said acidified juices to acid hydrolysis by heating them to a predetermined temperature under a pressure of from 40 to 125 p.s.i.g. for a fixed period of time to produce a hydrolyzate containing crude hecogenin; and separating said crude hecogenin from said hydrolyzate.

2. The process of claim 1 further comprising the step of:

extracting the sapogenins, hecogenin and tigogenin, from said crude hecogenin by means of an organic solvent.

3. The process of claim 2 wherein said organic solvent is heptane.

4. The process of claim 2 further comprising the steps of:

acetylating said sapogenins, hecogenin and tigogenin, to obtain an acetylation product; and recrystallizing said hecogenin from said acetylation product.

5. The process of claim 1 wherein said acidification and acid hydrolysis are carried out using sulfuric acid.

6. The process of claim 1 wherein said acidification and acid hydrolysis are carried out using hydrochloric acid.

7. The process of claim 1 wherein said acidification and acid hydrolysis are carried out using phosphoric acid.

8. The process of claim 1 wherein said predetermined temperature is in the range from 150° C. to 250° C.

9. The process of claim 1 wherein said fixed period of time is between 45 minutes and 3 hours.

10. A process for obtaining steroid content from saponin-containing juices of certain plant material, which process comprises:

acidifying said juices with sulfuric acid to a pH in the range of 0.4 to 1.5;

subjecting said acidified juices to acid hydrolysis by heating them to a temperature in the range of 150° C. to 250° C. at a pressure from 40 to 125 p.s.i.g. for between 45 minutes and 3 hours to produce a hydrolyzate containing crude hecogenin;

separating said crude hecogenin from said hydrolyzate;

extracting the sapogenins, hecogenin and tigogenin, from said crude hecogenin using heptane;

acetylating said sapogenins, hecogenin and tigogenin, to obtain an acetylation product; and recrystallizing said hecogenin from said acetylation product.

11. The process of claim 1 wherein said saponin-containing juices are collected undiluted from said plant material.

12. The process of claim 1 wherein said plant material consists of the leaves of *Agave sisalana*.

13. The process of claim 1 wherein said predetermined temperature is in the range from 150°C. to 250°C. and said fixed period of time is between 45 minutes and 3 hours.

14. The process of claim 1 wherein said pH is from 0.4 to 0.6.

* * * * *